(12) United States Patent
Plowman et al.

(10) Patent No.: US 8,619,257 B2
(45) Date of Patent: *Dec. 31, 2013

(54) RECOMBINANT BACTERIOPHAGE FOR DETECTION OF NOSOCOMIAL INFECTION

(75) Inventors: Thomas Edward Plowman, Cary, NC (US); Erica M. Phillips, Woodstock, GA (US); Richard Hantke, Chicago, IL (US); Daniel Baird, Woodstock, GA (US); Mike Rainone, Palestine, TX (US); Talbot Presley, Palestine, TX (US)

(73) Assignee: Kimberley-Clark Worldwide, Inc., Neenah, WI (US)

( * ) Notice: Subject to any disclaimer, the term of this patent is extended or adjusted under 35 U.S.C. 154(b) by 1594 days.

This patent is subject to a terminal disclaimer.

(21) Appl. No.: 11/955,779

(22) Filed: Dec. 13, 2007

(65) Prior Publication Data

US 2012/0143024 A1    Jun. 7, 2012

(51) Int. Cl.
*G01N 21/00* (2006.01)
*G01N 33/48* (2006.01)

(52) U.S. Cl.
USPC ............................................ 356/432; 356/39

(58) Field of Classification Search
USPC ............................................ 356/39–42, 432
See application file for complete search history.

(56) References Cited

U.S. PATENT DOCUMENTS

| | | | |
|---|---|---|---|
| 4,389,330 A | 6/1983 | Tice et al. | |
| 4,530,840 A | 7/1985 | Tice et al. | |
| 4,897,268 A | 1/1990 | Tice et al. | |
| 5,075,109 A | 12/1991 | Tice et al. | |
| 5,196,524 A | 3/1993 | Gustafson et al. | |
| 5,407,609 A | 4/1995 | Tice et al. | |
| 5,466,348 A | 11/1995 | Holm-Kennedy | |
| 5,491,084 A | 2/1996 | Chalfie et al. | |
| 5,625,048 A | 4/1997 | Tsien et al. | |
| 5,722,397 A * | 3/1998 | Eppstein | 600/345 |
| 5,777,079 A | 7/1998 | Tsien et al. | |

(Continued)

FOREIGN PATENT DOCUMENTS

EP    0482960 A1    4/1992
EP    1820517 A2    8/2007

(Continued)

OTHER PUBLICATIONS

Unge et al. "Simultaneous Monitoring of Cell Number and Metabolic Activity of Specific Bacterial Populations with a Dualgfp-luxAB Marker System" .Feb. 1999. American Society for Microbiology vol. 65 No. 2 pp. 813-821.*

(Continued)

*Primary Examiner* — Tara S Pajoohi Gomez
(74) *Attorney, Agent, or Firm* — Dority & Manning, PA

(57) ABSTRACT

Disclosed herein are methods and devices for detection of bacterial HAI. Disclosed methods may be utilized for continuous in vivo monitoring of a potential bacterial infection site and may be utilized to alert patients and/or health care providers to the presence of pathogenic bacteria at an early stage of infection. Disclosed methods include utilization of recombinant bacteriophage to deliver to pathogenic bacteria a translatable genetic sequence encoding an optically detectable marker or an enzyme capable of producing an optically detectable marker. Upon detection of the optical signal produced by the marker, medical personnel may be alerted to the presence of pathogenic bacteria at the site of inquiry. Any bacterial causative agent of HAI may be detected according to disclosed methods.

11 Claims, 3 Drawing Sheets

(56) References Cited

U.S. PATENT DOCUMENTS

| | | | |
|---|---|---|---|
| 5,804,387 A | 9/1998 | Cormack et al. | |
| 5,811,128 A | 9/1998 | Tice et al. | |
| 5,862,803 A | 1/1999 | Besson et al. | |
| 5,894,175 A | 4/1999 | Berlin et al. | |
| 5,919,445 A | 7/1999 | Chao | |
| 5,938,617 A * | 8/1999 | Vo-Dinh | 600/476 |
| 5,968,766 A | 10/1999 | Powers | |
| 6,013,284 A | 1/2000 | Samain et al. | |
| 6,146,826 A | 11/2000 | Chalfie et al. | |
| 6,289,238 B1 | 9/2001 | Besson et al. | |
| 6,322,783 B1 | 11/2001 | Takahashi | |
| 6,441,747 B1 | 8/2002 | Khair et al. | |
| 6,659,947 B1 | 12/2003 | Carter et al. | |
| 6,660,264 B1 | 12/2003 | Pasechnik et al. | |
| 6,802,811 B1 | 10/2004 | Slepian | |
| 7,087,226 B2 | 8/2006 | Ramachandran et al. | |
| 7,294,105 B1 | 11/2007 | Islam | |
| 2002/0000649 A1 | 1/2002 | Tilmans et al. | |
| 2003/0027241 A1 | 2/2003 | Saylor et al. | |
| 2004/0078219 A1 | 4/2004 | Kaylor et al. | |
| 2005/0003346 A1 | 1/2005 | Voorhees et al. | |
| 2005/0101841 A9 | 5/2005 | Kaylor et al. | |
| 2006/0159589 A1 | 7/2006 | Saxena | |
| 2007/0059725 A1 | 3/2007 | Voorhees | |
| 2007/0175278 A1 | 8/2007 | Puppels et al. | |
| 2007/0178450 A1 | 8/2007 | Wheeler et al. | |

FOREIGN PATENT DOCUMENTS

| | | |
|---|---|---|
| JP | 2002-515967 | 5/2002 |
| JP | 2002-541217 | 12/2002 |
| JP | 2004-283003 | 10/2004 |
| JP | 2007-517500 | 7/2007 |
| WO | WO 9420078 A1 | 9/1994 |
| WO | WO 9606638 A1 | 3/1996 |
| WO | WO97/17614 | 5/1997 |
| WO | WO2005/037856 | 4/2005 |
| WO | WO 2006086578 A1 | 8/2006 |

OTHER PUBLICATIONS

Edlund et al. "Degradable Polymer Microspheres for Controlled Drug Delivery" 2002 Advances of Polymer Science, vol. 157 pp. 67-112.*

Search Report and Written Opinion for PCT/IB2008/053655 dated Aug. 24, 2009, 13 pages.

Lakowicz, et al., "Emerging Biomedical and Advanced Applications of Time-Resolved Fluorescence Spectroscopy" *Journal of Fluorescence*, vol. 4, No. 1, 1994.

Abstract—Ackermann, "Bacteriophage Observations and Evolution." *Research in Microbiology*, 154.4 (2003): 245-251.

Abstract—Ackermann, "Frequency of morphological phage descriptions in 1995", *Archives of Virology*, vol. 141, No. 2, pp. 209-218, (1996).

Abstract—Ahmad, S.I., Treatment of post-burns bacterial infections by bacteriophages, specifically ubiquitous *Pseudomonas* spp. Notoriously resistant to antibiotics, *Medical Hypothesis*, vol. 58, Issue 4, Apr. 2002, pp. 327-331.

Awais, et al., "A Recombinant Bacteriophge-Based Assay for the Descriminative Detection of Culturable andViable by Nonculturable *Escherichia coli* O157:H7", *Biotechnol. Prog.*, 22, pp. 853-859, (2006).

Abstract—Barrow, et al., Bacteriophage therapy and prophylaxis: rediscovery and renewed assessment of potential, vol. 5, Issue 7, Jul. 1997, pp. 268-271.

Clark et al. "Bacteriophages and Biotechnology: Vaccines, Gene Therapy and Antibacterials." *Trends in Biotechnology* 24:5 (2006) pp. 212-218.

Dunlap, et al., "Control of *Vibrio fischeri* lux Gene Transcription by a Cyclic AMP Receptor Protein-LuxR Protein Regulatory Circuit", *Journal of Bacteriology*, Sep. 1988, p. 4040-4046.

Engebrecht et al. "Bacterial Bioluminescence: Isolation and Genetic Analysis of Functions from *Vibrio fischeri*." *Cel*,. 32.3 (1983): 773-781.

Abstract—Gross, et al., "Isolation of bacteriophages specific for the K1 polysaccharide antigen of *Escherichia coli*.", *Journal of Clinical Microbiology*, December, 6(6): 548-550 (1977).

Mangram, et al., "Guideline for Prevention of Surgical Site Infections, Centers for Disease Control and Prevention", vol. 20, No. 4 (1999).

Hansen, Ashlee. "Xylitol: A Dental Phenomenon." *The American Dental Hygienists' Association*, Aug. 2006. Aug. 7, 2008.

National Nosocomial Infections Surveillance (NNIS) Report, Data Summary from Oct. 1986-Apr. 1996, May 1996.

Loessner, et al., "Evaluation of Luciferase Reporter Bacteriophage A511::luxAB for Detection of *Listeria monocytogenes* in Contaminated Foods", *Applied and Environmental Microbiology*, Aug. 1977, pp. 2961-2965.

Mullaney, et al., "Green fluorescent protein as a probe of rotational mobility within bacteriophage T4", *Journal of Virol Methods*, Jul. 2008, 88(1):35-40.

Oda, et al., "Rapid Detection of *Escherichia coli* O154:H7 by Using Green Fluorescent Protein-Labeled PP01 Bacteriophage", *Applied and environmental Microbiology*, Jan. 2004, pp. 527-534.

Riska et al. "Specific Identification of *Mycobacterium tuberculosis* with the Luciferase Reporter Mycobacteriophage: Use of $p$-Nitro-$\alpha$-Acetylamion-$\beta$-Hydroxy Propiophenone." *Journal of Clinical Microbiology*, vol. 35 No. 12 (1997): 3225-3231.

Stewart et al. "The Specific and Sensitive Detection of Bacterial Pathogens Within 4 h Using Bacteriophage Amplification." *Journal of Applied Microbiology*. 84 (1998): 777-783.

Giana, et al. "Rapid Identification of Bacterial Species by Fluorescence Spectroscopy and Classification Through Principal Components Analysis", *Journal of Fluorescence*, 13 (2003), pp. 489-493.

Utzinger et al., "Fibre Optic Probes in Optical Spectroscopy, Clinical Applications," *Encyclopedia of Spectroscopy and Spectrometry*, Academic Press, pp. 512-528 (1999).

Utzinger et al., "Fiber optic probes for biomedical optical spectroscopy," *Journal of Biomedical Optics*, vol. 8, No. 1, pp. 121-147 (Jan. 2003).

Plowman et al., "Femtomolar sensitivity using a channel-etched thin film waveguide fluoroimmunosensor," *Biosensors & Bioelectronics*, vol. 11, No. 1/2, pp. 149-160 (1996).

Abstract—Plowman et al., "Multiple-Analyte Fluoroimmunoassay Using an Integrated Optical Waveguide Sensor (Abstract)," *Anal. Chem.* vol. 71, No. 19, pp. 4344-4352 (1999).

Plowman, "Silicon oxynitride integrated optical waveguide fluoroimmunosensor: multiple analyte sensing," Doctoral Dissertation, Duke University, 1999.

Plowman et al., "Surface sensitivity of SiON integrated optical waveguides (IOWs) examined by IOW-attenuated total reflection spectrometry and IOW-Raman spectroscopy," *Thin Solid Films*, vol. 243, pp. 610-615 (1994).

Plowman et al., "Waveguide Multi-Channel Immunoassay using Photo-Deprotection Immobilization," *SPIE* vol. 3603, pp. 163-169 (Jan. 1999).

Abstract—Yu et al. "Characterization of a Phage Specific to Hemorrhagic *Escherichia coil* O157:H7 and Disclosure of Variations in Host Outer Membrane Protein OmpC." *Journal of Biomedical Science*, 5 (1998): 370-382.

Hemorrahagic *Escherichia coli*O157:H7 and Disclosure of Variations in Host Outer Membrane Protein OmpC. *Journal of Biomedical Science*, 5 (1998): 370-382.

* cited by examiner

RECOMBINANT BACTERIOPHAGE FOR DETECTION OF NOSOCOMIAL INFECTION

BACKGROUND

Nosocomial or hospital acquired infection (HAI) has been estimated by the World Health Organization (WHO) to kill between 1.5 and 3 million people every year worldwide. Though commonly referred to as hospital acquired infections, nosocomial infections result from treatment in any healthcare service unit, and are generally defined as infections that are secondary to the patient's original condition. In the United States, HAIs are estimated to occur in 5 percent of all acute care hospitalizations, resulting in more than $4.5 billion in excess health care costs. According to a survey of U.S. hospitals by the Centers for Disease Control and Prevention (CDC), HAIs accounted for about 1.7 million infections and about 99,000 associated deaths in 2002. The CDC reported that "[t]he number of HAIs exceeded the number of cases of any currently notifiable disease, and deaths associated with HAIs in hospitals exceeded the number attributable to several of the top ten leading causes of death in U.S. vital statistics" (Centers for Disease Control and Prevention, "Estimates of Healthcare Associated Diseases," May 30, 2007).

HAIs, including surgical site infections (SSIs), catheter related blood stream infections (CRBSIs), urinary tract infections (UTIs), ventilator associated pneumonia (VAP), and others, may be caused by bacteria, viruses, fungi, or parasites. Infections acquired in a hospital setting are commonly caused by bacterial organisms, such as *Escherichia coli, Staphylococcus aureus*, and *Pseudomonas aeruginosa*. According to the CDC's Guideline for Prevention of Surgical Site Infections (1996), these species are ranked among the top five pathogens isolated from surgical site infections between 1986 and 1996. A ranking of the percentage distributions of infections that can be directly attributable to individual pathogen species may vary slightly between SSI, CRBSI, UTI, and VAP, but it is generally understood that less than about a dozen species are responsible for the vast majority of cases (see, e.g., National Nosocomial Infections Surveillance (NNIS) Report, Data Summary from October 1986-April 1996, May, 1996).

Ongoing efforts are being made to prevent HAI through, for instance, improved hand washing and gloving materials and techniques, but such efforts have met with limited success. In an effort to better understand and curb HAIs, government regulations have increased pressure on hospitals and care-givers to monitor and report these types of infections. However, these measures are further complicated due to the prevalence of outpatient services, a result of which being that many HAIs do not become evident until after the patient has returned home. As such, infection may proceed undiagnosed for some time, complicating treatment and recovery.

A need currently exists for improved methods for diagnosing HAI. Moreover, methods that could monitor a patient in an outpatient setting, for instance a patient's home, would be of great benefit.

SUMMARY

In accordance with one embodiment, a method for detecting the presence or amount of a pathogenic bacterium that is a source of a hospital acquired infection is disclosed. For example, a method may include locating a recombinant bacteriophage in an in vivo environment. The recombinant bacteriophage may carry exogenous genetic material encoding a protein that is capable of directly or indirectly producing an optically detectable signal.

Upon binding of the recombinant bacteriophage to the pathogenic bacterium, the genetic material from the bacteriophage may be transferred to the pathogenic bacterium and the bacterium may begin to express the protein. In one embodiment, the protein can directly produce the optically detectable signal. For instance, the protein can emit an optically detectable signal upon excitation. In another embodiment, the protein can interact with a cofactor to form a detectable marker that directly produces the optically detectable signal.

Upon emission, the optically detectable signal may be transmitted through a fiber optic cable to a detector and the presence or amount of the pathogenic bacterium in the environment may be determined.

In another embodiment, disclosed is a portable device for detecting the presence or amount of a pathogenic bacterium. A device may include a portable enclosure that may carry a power source, an optical detector, a signal processor, and a signaling device for emitting a signal upon detection of the pathogenic bacterium in an environment. The device may also include a connecting device for attaching the enclosure to the clothing or body of a wearer and a fiber optic cable that extends beyond the enclosure that is for inserting into the environment of inquiry. In particular, the fiber optic cable may be in optical communication with the optical detector. In addition the fiber optic cable may carry recombinant bacteriophages in a delivery vehicle applied to at least a portion of a surface of the fiber optic cable.

Other features and aspects of the present disclosure are discussed in greater detail below.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which.

Figure 1:
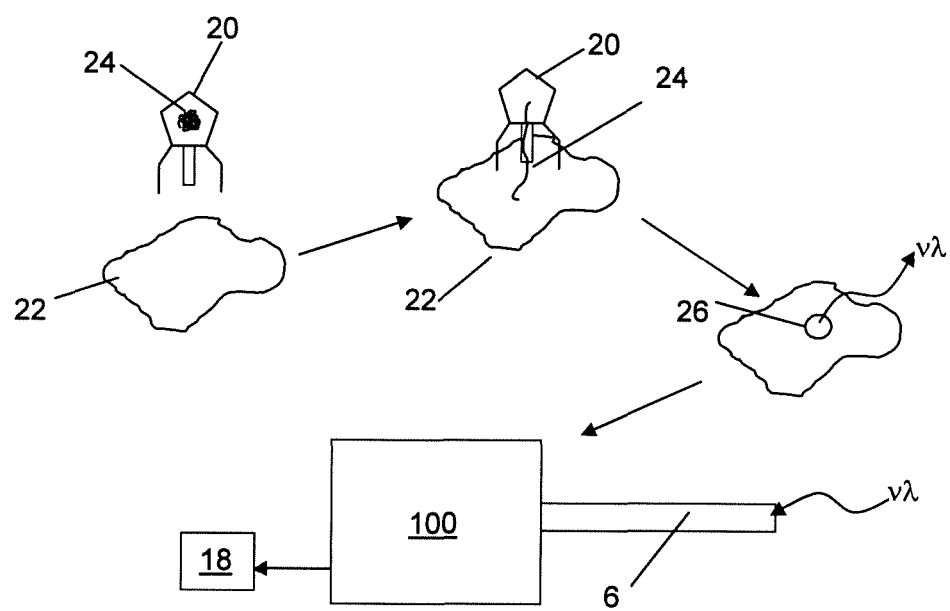
FIG. 1 is a schematic representation of one embodiment of a bacterial detection process as described herein.

Repeat use of reference characters in the present specification and drawings is intended to represent same or analogous features or elements.

DETAILED DESCRIPTION OF REPRESENTATIVE EMBODIMENTS

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment, may be used on another embodiment to yield a still further embodiment. Thus, it is intended that the present disclosure covers such modifications and variations as come within the scope of the appended claims and their equivalents.

The present disclosure is generally directed to methods for detection of bacterial HAI. In one embodiment, disclosed methods may be utilized for continuous in vivo monitoring of a potential bacterial infection site and may be utilized to alert patients and/or health care providers to the presence of pathogenic bacteria at an early stage of infection, thereby providing for earlier intervention and improved recovery rates from bacterial infection. In another embodiment, disclosed methods may be utilized for in vitro testing protocols to determine the presence of pathogenic bacteria in fluid or tissue samples obtained from a patient.

Presently disclosed methods include utilization of a recombinant bacteriophage to deliver to a pathogenic bacterium a translatable genetic sequence encoding a protein that may directly or indirectly produce an optically detectable signal. More specifically, the genetic sequence may encode an optically detectable marker or an enzyme capable of producing an optically detectable marker. In general, any bacterial source of HAI may be detected according to disclosed methods. For instance, while *Escherichia coli, Staphylococcus aureus*, and *Pseudomonas aeruginosa* may be of particular interest in certain embodiments, disclosed methods are not limited to these bacteria. Other common bacterial sources of HAI that may be detected according to disclosed methods include, without limitation, coagulase-negative staphylococci, *Enterococcus* spp., *Enterobacter* spp., *Klebsiella pneumoniae, Proteus mirabilis, Streptococcus* spp., and so forth.

An optically detectable marker that may be used to determine the presence of a bacterial pathogen may include a protein that is directly produces an optically detectable signal upon formation and excitation of the protein. For instance, a fluorescent protein such as green fluorescent protein (GFP) or a related variant may be utilized as a detectable marker. The green fluorescent protein is a protein comprised of 238 amino acids (26.9 kDa), originally isolated from the jellyfish *Aequorea victoria/Aequorea aequorea/Aequorea forskalea*, which fluoresces green when exposed to blue light. Green fluorescent proteins and their uses are known in the art. For instance, U.S. Pat. No. 5,491,084 to Chalfie, et al. (incorporated herein by reference) discloses various uses of a green fluorescent protein, together with host cells having gene constructs encoding a GFP. U.S. Pat. Nos. 5,625,048 and 5,777,079 both to Tsien, et al. (both incorporated herein by reference) disclose modified GFPs having emission and excitation spectra different to those of wild-type GFPs. U.S. Pat. No. 5,804,387 to Cormack, et al. (incorporated herein by reference) discloses GFP mutants having modified excitation and emission spectra.

Another example of a detectable marker that may be encoded by a recombinant phage for utilization as described herein is aequorin. Aequorin is composed of two subunits, the apoprotein apoaequorin and the prosthetic group coelenterazine. In the presence of molecular oxygen, the subunits form the functional protein that upon binding of calcium ion undergoes a conformational change and through oxidation converts to excited coelenteramide and carbon dioxide. Upon relaxation of the coelenteramide to its ground state, blue light is emitted.

In one embodiment, a protein may be encoded by a recombinant bacteriophage that may indirectly produce the optically detectable signal. For instance, an optically detectable marker may be a product of an enzyme-catalyzed reaction and may formed and emit an optically detectable signal upon interaction of a chemical cofactor with the enzyme. According to this embodiment, a recombinant phage may encode an enzyme that may interact with a cofactor to produce the detectable marker. For instance, a recombinant phage may encode an enzyme such as bacterial luciferase. Bacterial luciferase is a mixed function oxidase formed by the association of two protein subunits, α and β. The subunits associate to form a 2-chain complex that catalyzes the flavin-mediated hydroxylation of a long-chain aldehyde (e.g., luciferin) to yield carboxylic acid and an excited flavin. Upon the decay of the flavin to ground state, an optically detectable signal is emitted.

According to disclosed methods, a recombinant bacteriophage can be utilized to deliver genetic material to a targeted bacterial pathogen. A bacteriophage is a mobile genetic element specifically attracted to bacterial cells. Most phages are a few hundred nanometers in length and include a hexagonal base plate, tail pins, and tail fibers, all of which are involved in the specific binding of a phage to surface receptors of a bacterium. Following the irreversible binding of a phage to a bacterium, the sheath of the phage contracts and a hollow core is injected through the bacterial envelope, allowing the contents of the head (primarily genetic nucleic acids) to be injected into the bacterium. The foreign nucleic acids become incorporated into the host DNA and commandeer the cellular bio-machinery to replicate the genetic code of the phage.

Accordingly, a specific bacteriophage for a targeted bacterium may be utilized as a delivery vehicle for genetic material encoding an optically detectable marker or an enzyme capable of producing an optically detectable marker. A wide variety of bacteriophages are available for any given bacterial cell from, for example, the American Type Culture Collection (ATCC, P.O. Box 1549 Manassas, Va., USA) or by isolation from natural sources that harbor the host cells. A list of phage types has been published as the Catalogue of Bacteria & Bacteriophages (ATCC, Rockville, Md. 1989). Specific phages for over 100 bacterial genera have been isolated (Ackermann, 1996 Arch Virol., 141:2, 209-18.). Other microorganism depositories are also known in the art.

Specific phages may include, without limitation, *Escherichia* phages (lambda, M13, mp 18, MS2, Mu, P1, PhiX174, QB, R17, T1, T2, T3, T4, T5, T6, T7, U3), Psudomonas phages (Psp1, Psp2, Psp3, Psp4, Psp5, 73, 119X, B3, D3, EL, F8, F10, F116, gh-1, LKA1, LKD16, M6, PA11, PaP2, PaP3, Pf1, Pf3, phi6, phi8, phi12, phi13, phiCTX, phiKMV, phiKZ, PP7, PRR1), *Staphylococcus* phages (94, S1, S2, S3, S4, S5, S6, S7, phiNM1, phiNM2, phiNM3, phiNM4, 3A, 11, 29, 37, 42E, 47, 52A, 53, 55, 66, 69, 71, 77, 80, 85, 88, 92, 96, 187, 2638A, CNPH82, EW, G1, K, PH15, phil3, phil2, phiETA2, phiETA3, phiETA, phiPVL108, phiSLT, PT1028, PVL, ROSA, SAP-2, Twort, X2), *Enterobacter* phages (186, 933W, a3, ES18, f1, fd, F14184b, fr, G4, HKD22, HK97, HK620, 12-2, ID1, ID8, ID11, ID12, ID22, ID34, ID41, ID45, ID52, If1, Ike, JK06, K1-5, K1E, KIF, KU1, L17, lambda, M13, Mu, MX1, N4, N15, NC1, NC2, NC5, NC6, NC7, NC10, NC11, NC13, NC16, NC19, NC37, NC41, NC51, NC56, NL95, P2, P4, P7, P22, Phil, phiK, phiP27, phiX174, PR3, PR4, PR5, PR772, PRD1, PsP3, RP32, RB43, RTP, S13, Sf6, SP6, SP, ST104, T1, T3 (strain Luria), T4, T5, T5 (strain ATCC 11303-B5), T7, VT2-Sakai, WA2, WA3, WA4, WA5, WA6, WA10, WA11), *Enterococcus* phages (phiEF24C), and *Streptococcus* phages (2972, 7201, Cp-1, DT1, MM1, MM1 1998, 01205, P9, phi3396, Sfi11, Sfi19, Sfi21, SMP).

Other bacteriophages with a high level of specificity for a particular bacterial pathogen may be developed. For instance, methods for screening samples for specific bacteriophage as have been described in U.S. Pat. No. 6,322,783 to Takahashi, which is incorporated herein by reference, may be utilized to develop specific bacteriophage for utilization as described herein.

A bacteriophage utilized as described herein may be a recombinant phage that has been engineered to include exogenous translatable genetic code. Recombinant bacteriophages may be prepared or obtained according to any means as is generally known in the art. In general, a recombinant bacteriophage may include an inserted DNA cassette that allows for translation and transcription of a DNA sequence, e.g., a cDNA sequence, which may in one embodiment encode an optically detectable protein.

A DNA cassette may include any DNA that encodes a protein in a sense orientation. For instance, constructs suitable for use in the disclosed process may encode any GFP, luciferase, aequorin, or other materials as discussed above.

DNA cassettes encoding GFPs are known in the art that may be incorporated into a recombinant phage. For example, U.S. Pat. Nos. 6,146,826 and 5,491,084, to Chalfie, et al., both of which are incorporated herein by reference, describe DNA sequences that may encode a GFP for use in forming a recombinant bacteriophage.

When considering a detectable marker as may be formed through action of an enzyme such as luciferase, which is a multiunit protein, a single DNA cassette may encode all of the subunits of the protein or optionally multiple cassettes may be inserted into the bacteriophage DNA, as is generally known in the art. For example, a single construct encoding a fusion luciferase luxAB gene, as is described by U.S. Pat. No. 5,196,524 to Gustafson, et al., incorporated herein by reference, may be utilized in forming a recombinant bacteriophage.

In those embodiments in which a detectable marker may be developed upon interaction of the encoded protein with a proteinaceous cofactor, a recombinant phage may encode the cofactor as well as the enzyme. For example, genetic material of a recombinant phage may encode a luciferin substrate, in addition to one or both subunits of a luciferase enzyme. Genetic material encoding a cofactor may be provided to a bacteriophage in the same or in a different DNA cassette as is utilized to provide genetic material encoding the primary protein. For example, in one embodiment, a recombinant bacteriophage may include a single DNA cassette that encodes both subunits of a luciferase protein as well as a luciferin substrate for the enzyme. In one embodiment a recombinant phage including a lux DNA cassette derived from the marine bacterium *Vibrio fischeri* as described by Engebrecht, et al. (*Cell*, 32:3, 1983, 773-781) and U.S. Published Patent Application No. 2003/0027241 to Savior, et al., both of which are incorporated herein by reference, may be utilized. In this particular embodiment, the complete cassette may encode five genes, luxA, luxB, luxC, luxD, and luxE. LuxA and luxB encode the α and β subunits of the protein, as discussed above, while luxC and luxD encode a luciferin aldehyde substrate.

In addition to DNA encoding the primary protein, e.g., a GFP, a luciferase, or a subunit thereof in a sense orientation, a DNA cassette may also include suitable operably linked regulatory sequences as are generally known to those of skill in the art. For instance, a DNA cassette may include DNA encoding one or more of a suitable translation leader sequence, a promoter, and polyadenylation and transcription termination sequences.

Methods for forming recombinant bacteriophage and suitable vectors and plasmids as may be utilized in formation processes are generally known to those of skill in the art. For instance, delivery of DNA to bacteria using recombinant bacteriophage have been described, for example by Clark, et al. (Trends in Biotechnology, 24(5):2122-218) and by Westwater, et al. (Microbiology 148 (pt4):943-950). Similarly, recombinant luciferase reporter phages and methods for forming such are generally known to those in the art (see, e.g., Riska, et al., J. Clin. Microb., December 1997, 3225-3231).

A recombinant bacteriophage may include other added genetic material as well. For instance, under normal circumstances, a bacterium that has been infected with the DNA of a bacteriophage will lyse following a period of time, leading to spread of the replicated phage. According to presently disclosed methods, it may be preferred in some embodiments to prevent the lysing of the infected bacteria, for instance so as to provide for an increased concentration of detectable markers as well as to limit release of endotoxins and/or virulence factor from bacteria upon lysing. As such, recombinant phages for use as disclosed herein may be subjected to additional genetic manipulation so as to prevent lysing of bacteria following insertion of the phage genetic material into a bacterium. For instance, U.S. Pat. No. 7,087,226 to Ramachandran, et al. (incorporated herein by reference) describes lysin-deficient bacteriophages that are incapable of facilitating efficient lysis of the bacterial host.

In accord with disclosed methods, recombinant bacteriophages may be located in an environment in which the targeted bacteria may exist to detect the presence of the pathogens in the environment. For instance, one or more recombinant bacteriophages as described herein may be located in vivo at a potential bacterial infection site such as a wound, a catheter site, a surgical drain site, an endotracheal (ET) tube site, or the like. In another embodiment, bacteriophages may be located in an in vitro environment in conjunction with a tissue or fluid sample from a patient. The in vitro environment may be controlled so as to encourage existence of any living bacteria in the sample such that the bacteria may be genetically transformed by the phages and subsequently emit an optically detectable signal.

FIG. 1 schematically illustrates one embodiment of a detection regime. According to this particular detection method, a recombinant bacteriophage 20 including genetic material 24 that encodes for a detectable marker may specifically bind a pathogenic bacterium 22. Following initial binding, the genetic material 24 of the bacteriophage 20 may be inserted into and taken up by the bacterium 22 upon which the biomachinery of the bacterium may transcribe the genetic code and produce the detectable marker. The optical signal produced by the detectable marker (νλ) may be detected, as with a device 100 described at more length below, and appropriate notification may be obtained from the device 100. Following notification, suitable medical intervention against the pathogen may be instituted.

Disclosed methods may be utilized to simultaneously detect a plurality of different pathogens. For instance, a plurality of recombinant bacteriophages specific for different bacterial pathogens may be located at a potential infection site or in an in vitro environment in which the pathogenic bacteria may exist. The recombinant bacteriophages may be engineered to encode for the same detectable markers or for different detectable markers, as desired. For instance, a plurality of different phages may all encode the same detectable marker. Upon detection of the marker, a medical professional may be alerted to the presence of a pathogen at the site of interest, signaling the need for further investigation to determine the specific bacteria involved. In another embodiment, different phages may encode different markers. According to this embodiment, determination of the characteristics of a detected signal may provide information regarding the specific bacteria involved in the infection. Optionally, combinations of the two approaches may be used. For instance, a class of phages, for example all phages specific to members of a first genus, e.g., *Escherichia*, may encode a first detectable marker, and all phages specific to members of a second genus, e.g., *Staphylococcus*, may encode a second detectable marker. Accordingly, the subsequent detection of an emitted optical signal may inform medical personnel as to the general type of bacterial infection, though the determination of the specific pathogen involved may require additional investigation.

In general, recombinant bacteriophages may be delivered to the targeted site via any suitable delivery vehicle. For instance, a liquid vehicle, e.g., a sterile saline solution, may be utilized as a delivery vehicle and the liquid mixture including the bacteriophages may be simply applied to the site of inquiry. A simple liquid delivery vehicle may be preferred for certain in vitro detection methods. For instance a biological sample of interest such as, e.g., wound fluid, blood, serum, vaginal fluid, urine, or the like, that has been obtained from a patient may be combined with a liquid including recombinant bacteria. The mixture may be cultured in vitro under conditions to encourage the uptake of the phage genetic material by any bacteria present in the sample (e.g., following a culturing period of between about 30 minutes and about 4 hours, or longer in other embodiments, generally depending upon the characteristics of the bacteria involved), following which the sample may be examined for signals produced by detectable markers.

In other embodiments, for instance certain in vivo applications, other delivery vehicles may be preferred. For instance, a delivery vehicle may be utilized that may maintain the recombinant bacteriophage for a period of time at the site of interest, e.g., within a wound, a drain insertion site, or the like.

In one embodiment a delivery vehicle may be hydrophilic in nature. This may be preferred in certain in vivo detection processes, as a hydrophilic delivery vehicle may be less likely to provoke an immuno-suppression response. This is not a requirement of the invention, however, and in other embodiments, the delivery vehicle may include a hydrophobic material, e.g., a hydrophobic polymeric matrix.

A delivery vehicle may include a degradable polymeric matrix, such as, in one embodiment, a hydrogel. For instance, a delivery vehicle may include a biocompatible hydrogel that may be located at an in vivo site of interest. Hydrogels generally include polymeric matrices that may be highly hydrated, e.g., from about 20% to more than 99% water by weight, while maintaining structural stability of the matrix. Suitable hydrogel matrices may include un-crosslinked and crosslinked hydrogels. In addition, crosslinked hydrogel delivery vehicles may include hydrolyzable portions, such that the matrix may be degradable when utilized in an aqueous environment. For example, a delivery vehicle may include a cross-linked hydrogel including a hydrolyzable cross-linking agent, such as polylactic acid, and may be degradable in vivo. A degradable delivery vehicle may also be formed so as to have predetermined rate of degradation following location of the vehicle at an in vivo site of interest, i.e., a sustained release delivery vehicle having a predetermined rate of degradation.

Biodegradable polymeric matrices, including hydrogels, may include natural biopolymers such as glycosaminoglycans, polysaccharides, proteins, and so forth, as well as synthetic polymers, as are generally known in the art. A non-limiting list of polymeric materials that may be utilized in forming a hydrogel delivery vehicle may include, without limitation, dextran, hyaluronic acid, chitin, heparin, collagen, elastin, keratin, albumin, polymers and copolymers of lactic acid, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins and peptides, and so forth.

Biodegradable polymeric matrices, including hydrogels, may be formed according to any method as is generally known in the art. For instance, a hydrogel may self-assemble upon mere contact of the various components or upon contact in conjunction with the presence of particular environmental conditions (such as temperature or pH). Alternatively, assembly may be induced according to any known method following mixing of the components. For example, step-wise or chain polymerization of multifunctional monomers, oligomers, or macromers may be induced via photopolymerization, temperature dependent polymerization, and/or chemically activated polymerization. Optionally, a hydrogel may be polymerized in the presence of an initiator. For example, a hydrogel may be photopolymerized in the presence of a suitable initiator such as Irgacure® or Darocur® photoinitiators available from Ciba Specialty Chemicals. In another embodiment, a cationic initiator may be present. For example, a polyvalent elemental cation such as $Ca^{2+}$, $Mg^{2+}$, $Al^{3+}$, $La^{3+}$, or $Mn^{2+}$ may be used. In yet another embodiment, a polycationic polypeptide such as polylysine or polyarginine may be utilized as an initiator.

The components of the delivery vehicle may also be designed so as to provide a self-assembling matrix. For example, a hydrogel precursor may be administered to a patient in conjunction with one or more recombinant bacteriophages, and the hydrogel matrix may self-assemble at physiological conditions following administration of a precursor. For instance, a hydrogel precursor may include self-assembling biopolymers such as collagens, laminins, pro-elastin peptides, and so forth. A self-assembling hydrogel precursor may include synthetic polymers that may array themselves according to domains, as is generally known in the art. For example, hydrophilic, relatively charge-neutral synthetic polypeptides such as polyglycine or polylysine may be modified to function in this capacity. Polypeptides may be crosslinked by using carboxy-activating crosslinking agents such as water-soluble carbodiimides. Such cross-linking agents may be used to attach self-assembling proteins or other self-assembling macromolecules to the polypeptides. One example of this approach includes formation of a carbodiimide linkage of collagen or laminin with polylysine. Other hydroxylated entities may be linked in a similar manner. For example, polyvinyl alcohol may be linked with polypeptides using an epoxy-activation approach or crosslinked via polymerizable methacrylate groups along its side chains, as is known in the art.

In another embodiment, a self-assembling biodegradable polymeric matrix may be generated by use of precursors that have been derivatized to contain favorably reactive groups. For example, a hydrogel of this type may assemble using a first precursor derivatized with a particular reactive moiety and a second precursor derivatized with or comprising a second moiety that may preferentially react with the first moiety on the first precursor. Likewise, other such hydrogels could be generated using such reactive pairs wherein the two moieties that react to form the bond are each conjugated to the same or a different type of polymer. For example, the pairs may be antibody-antigen pairs or avidin-biotin (e.g. streptavidin-biotin).

In other embodiments a delivery vehicle need not include a self-assembling matrix. For example, a degradable matrix delivery vehicle incorporating one or more recombinant bacteriophages may be administered to a patient according to a suitable administration method following assembly of the matrix. For instance, a hydrogel delivery vehicle may be loaded with a recombinant phage, either via formation of the hydrogel in the presence of the phage, via absorption of the phage into the hydrogel along a concentration gradient, or according to any other suitable method, and the loaded hydrogel may then be located at a potential bacterial infection site.

As is known in the art, delivery vehicles may be formed to degrade over time. Accordingly, bacteriophages may be released to a site of interest as the delivery vehicle, e.g., the hydrogel, degrades over time, providing a sustained release effect at the site and lengthening the term for examination of the site as compared to a delivery system in which all of the bacteriophages are available at a single time to interact with pathogenic bacteria.

A delivery vehicle does not require a hydrogel component. For instance, a delivery vehicle may include a biodegradable polymeric coating that may encapsulate recombinant bacteriophages for release into the site of interest following location of the vehicle at a site of interest. For example, a delivery vehicle may include a biodegradable microparticle that encapsulates the recombinant phages. Recombinant phages may be held within a microparticle in conjunction with a hydrogel or other secondary carrier, but this is not a requirement. Biodegradable coatings as may be utilized may include, for instance, coatings including polylactide, polyglycolide, poly(lactide-co-glycolide), polyacrylate, polyanhydride, latex, starch, cellulose, dextran, hydroxypropylmethyl cellulose, polyorthoester, polycaprolactone, polyphosphazene, polysaccharide, proteinaceous polymers such as gelatin and fibrin, soluble derivatives of polysaccharides, soluble derivatives of proteinaceous polymers, polypeptides, polyester, polyorthoesters, and so forth, or mixtures or blends of any of these. Exemplary biodegradable microspheres are disclosed, for example, in U.S. Pat. Nos. 4,897,268; 5,075,109; 5,811,128; and 5,407,609 to Tice, et al., all of which are incorporated herein by reference.

Polysaccharides may include, for example poly-1,4-glucans, e.g., starch glycogen, amylose, amylopectin, and mixtures thereof. A biodegradable hydrophilic or hydrophobic polymer may be a water-soluble derivative of a poly-1,4-glucan, including hydrolyzed amylopectin, hydroxyalkyl derivatives of hydrolyzed amylopectin such as hydroxyethyl starch (HES), hydroxyethyl amylose, dialdehyde starch, and so forth.

Preferred delivery vehicles may depend upon the specific application of the detection scheme. For instance, as polylactic acid may exhibit a relatively long degradation period, e.g., about one year in vivo, this particular homopolymer may be utilized in circumstances where such a degradation rate is desirable and/or acceptable.

Other illustrative delayed-release carriers may include particles that include recombinant phages encapsulated in a non-liquid hydrophilic core (e.g., a cross-linked polysaccharide or oligosaccharide) and, optionally, an external layer comprising an amphiphilic compound, such as a phospholipid (as described by e.g., PCT Published Patent Application WO 94/20078 to Daniel, et al., U.S. Pat. No. 5,894,175 to Perrin, et al., and PCT Published Patent Application WO 96/06638 to Didier, et al., all of which are incorporated herein by reference).

Microcapsules may be prepared, for example, by dissolving or dispersing recombinant bacteriophages in an organic solvent and dissolving the polymer carrier material in the solvent. Following, the solvent containing the recombinant phages and the polymer may be dispersed in a continuous-phase processing medium. Following evaporation of a portion of the solvent, microcapsules may form containing the recombinant phages in suspension. Remaining solvent may then be extracted from the microcapsules. Exemplary formation procedures are described in more detail in U.S. Pat. Nos. 4,389,330 and 4,530,840, hereby incorporated by reference.

A delivery vehicle may carry materials in addition to recombinant bacteriophages. For instance, in those embodiments in which the detectable marker may be produced in the presence of a cofactor, a delivery vehicle may carry the cofactor, such that upon formation of the primary protein, the requisite cofactor may be in the vicinity, and the detectable marker and optically detectable signal may be generated.

A delivery vehicle may be located at a site according to any suitable method. For instance, recombinant bacteriophages in conjunction with a delivery vehicle, e.g., a liquid, a hydrogel, microparticles, etc., may be simply located at the site of interest during a medical procedure. For instance, prior to closing a surgical site, a delivery vehicle loaded with recombinant phages as described herein may be located at the site.

In one embodiment, bacterial phages may be delivered to a site of interest in conjunction with a medical device. For instance a delivery vehicle, e.g., a gel, may be applied to the surface of a medical device such as a catheter, a surgical drain, an ET tube, or the like, and the medical device may then aid in maintaining the delivery vehicle and the recombinant phages held therein at the site of interest.

Upon generation of a detectable signal, a sensor may be utilized to detect and transmit the signal to appropriate personnel. For example, in one preferred embodiment, disclosed methods may utilize a fiber optic-based sensor, one or more fiber optic cables of which may be located at a potential infection site. Optionally, a fiber optic cable of a sensor may carry a delivery vehicle that in turn may carry recombinant bacteriophages as described herein.

Beneficially, optical fibers may be formed of biocompatible materials that may remain at a site of interest for a relatively long period of time, for instance to monitor the site for infection throughout the healing process and until high potential for bacterial infection has past. For instance, when considering detection of SSI, it may be beneficial to monitor the site for infection for a period of up to about 30 days following surgery. When detecting other types of infection, a longer or shorter time period may be preferred. For example, when considering detection of CRBSI, monitoring may continue for the entire time a venous catheter is held in place, anywhere from a few hours up to several weeks. For instance, between about 72 hours and about 96 hours. In addition, at the time of removal, optical fibers may be easily removed from the site without the necessity of causing excessive tissue damage at the site, due to the small cross-section of the fibers.

Figure 2:
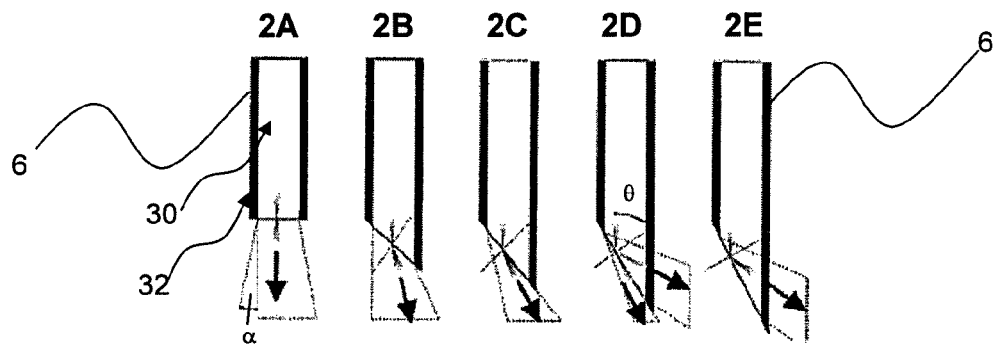
FIGS. 2A-2E are illustrative examples of optical fiber designs that are encompassed in the present disclosure.

FIG. 2 schematically illustrates several embodiments of optical fibers as may be utilized in a sensor according to certain disclosed detection methods. An optical fiber may include a core 30, through which light may travel, and an external cladding layer 32. The difference in the index of refraction between the core material and the clad material defines the critical angle $\theta$ at which total internal reflection takes place at the core/clad interface. Thus, light that impinges upon the interface at angle greater than the critical angle is completely reflected, allowing the light to propagate down the fiber.

Optical fibers may generally include multi-mode fibers having a core diameter greater than about 10 micrometers (µm). The preferred core diameter in any particular embodiment may depend upon the characteristics of excitation light (when required) and/or emission light, among other system parameters. For instance, in those embodiments in which a laser is the excitation source, a core diameter may be between about 50 µm and about 100 µm, or about 80 µm in one embodiment. In other embodiments, for instance, in those embodiments in which an excitation light source produces less coherent radiation, such as a multi-wavelength light emitting diode (LED), for example, it may be preferable to utilize an optical fiber having a larger core diameter, for instance between about 90 µm and about 400 µm.

The core/clad boundary of the fibers may be abrupt, as in a step-index fiber, or may be gradual, as in a graded-index fiber. A graded-index fiber may be preferred in some embodiments, as graded index fibers may reduce dispersion of multiple modes traveling through the fiber. This is not a requirement of disclosed sensors, however, and step-index fibers may alternatively be utilized, particularly in those embodiments in which the optical fiber is of a length such that dispersion will not be of great concern.

Optical fibers may be formed of sterilizable, biocompatible materials that may be safely placed and held at a potential infection site, and in one particular embodiment, at a surgical site. For example, optical fibers formed of any suitable type of glass may be used, including, without limitation, silica glass, fluorozirconate glass, fluoroaluminate glass, any chalcogenide glass, or the like may form the core and/or the clad.

Polymer optical fibers (POF) are also encompassed by the present disclosure. For instance, optical fibers formed of suitable acrylate core/clad combinations, e.g., polymethyl methacrylates, may be utilized. It may be preferred in some embodiments to utilize a multi-core POF so as to lower losses common to POF due to bending of the fiber. For instance, this may be preferred in those embodiments in which the optical fiber(s) of the sensor are in a non-linear conformation during use.

The end of a fiber may be shaped as desired. For instance, and as illustrated in FIGS. 2A-2E, polishing or otherwise forming a specific angle at the end face of a fiber may maintain the acceptance angle α and collection efficiency of the fiber, while rotating the field of view of the fiber, as depicted by the arrows on FIGS. 2A-2E. Depending upon the angle at the fiber end, light may enter the fiber from angles up to about 90° of the fiber axis (e.g., as shown at FIG. 2E) (see, e.g., Utzinqer, et al., Journal of Biomedical Optics, 8(1):121-147, 2003).

Optical fibers of a sensor may be formed so as to detect light at locations along the length of the fiber, in addition to at the terminal end of the fiber. For instance, at locations along the length of the fiber may be bent or notched so as to allow light through the clad, optionally at a predetermined angle, such that excitation light (when needed) and detectable signals emitted due to the presence of transformed bacteria may enter the optical fiber at these locations. For example, the clad of a fiber may be bent or otherwise notched at a predetermined angle to form a 'window' in the fiber. Thus, a single optical fiber may detect signals from transformed bacterial over a larger area.

A fiber optic sensor for use as described herein may include a fiber optic cable comprised of a single optical fiber or a plurality of optical fibers, depending upon the specific design of the sensor. For instance, a plurality of optical fibers may be joined to form a single fiber cable of a size to be located at an in vivo site of interest (e.g., less than about 1.5 mm in cross-sectional diameter).

Figure 3A:
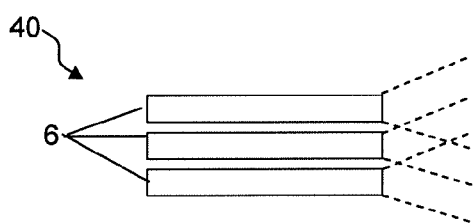
FIGS. 3A-3C are schematic representations of an optical fiber bundle as may be incorporated in a device as disclosed herein.
Figure 3B:
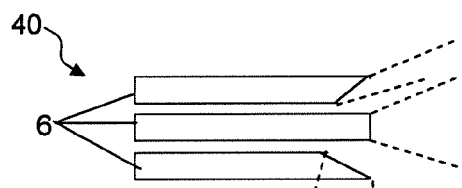
Figure 3C:
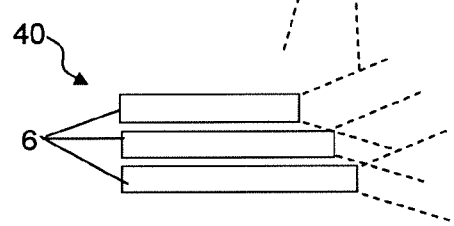

When utilizing a plurality of fibers in a fiber bundle or cable, individual fibers may be formed and arranged in relation to one another so as to provide a wider angle of detection. For instance, FIGS. 3A-3C illustrate several different embodiments of a fiber optic cable 40 comprising multiple optical fibers 6 in a bundle. For instance, as shown at FIG. 3A, through location of a plurality of fiber ends at a single cross-sectional area, improved light collection may be attained, as the total field area covered by the combined fibers will be larger than that for a single fiber. In the embodiment illustrated in FIG. 3B, the geometry of the end face of different fibers contained in the cable 40 may be different from one another, so as to allow light collection from a variety of different directions. In the embodiment illustrated in FIG. 3C, fiber ends are staggered over a length, so as to increase the axial length of the light collection area and increase the area of inquiry in an axial direction. Of course, combinations of such designs, as well as other fiber design for improving the collection of a signal area, including methods as discussed above as well as methods as are generally known to those in the art, may be utilized as well.

A fiber optic bundle or cable of optical fibers 40 may generally be held as a cohesive unit with any biocompatible sheath that can hold the unit together while maintaining flexibility of the fibers. For instance, a fiber optic cable may include an outer sheath of a flexible polyurethane.

Figure 4:
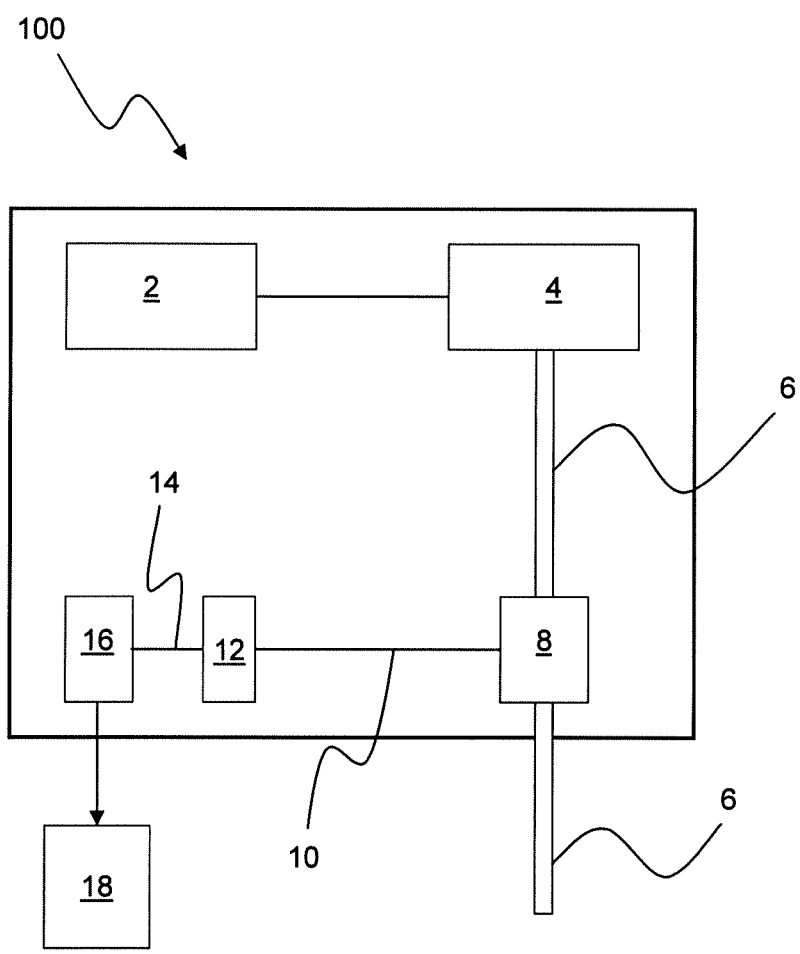
FIG. 4 is a schematic representation of a portion of a portable device as described herein.

In accordance with the present technology, one or more optical fibers may be utilized as a portion of a sensor that can be contained by use of a portable device, one embodiment of which is schematically illustrated in FIG. 4. As may be seen in FIG. 4, device 100 can include several components that may be housed within an enclosure 20.

Enclosure 20 may be, for example, a molded plastic enclosure of a size so as to be easily carried by or attached to a patient. For instance, enclosure 20 may include clips, loops, or the like so as to be attachable to a patient's clothing or body. In one embodiment, enclosure 20 may include a biocompatible adhesive at a surface, and may be adhered directly to a patient's skin. In general, enclosure 20 may be relatively small, for instance less than about 10 cm by about 8 cm by about 5 cm, so as to be inconspicuously carried by a patient and so as to avoid impedance of a patient's motion. Enclosure 20 may completely enclose the components contained therein, or may partially enclose the components contained therein. For example, enclosure 20 may include an access port (not shown) that may provide access to the interior of enclosure 20. In one embodiment, an access port may be covered with a removable cover, as is known in the art.

A first component as may be held within enclosure 20 is power supply 2 that may be configured in one embodiment to supply power to an excitation source 4 as well as other of the operational components as will be later described. In an exemplary configuration, power supply 2 may correspond to a battery, however those of ordinary skill in the art will appreciate that other power supplies may be used including those that may be coupled to an external alternating current (AC) supply so that the enclosed power supply may include those components necessary to convert such external supply to a suitable source for the remaining components requiring a power source.

As previously noted, power supply 2 may be configured in one embodiment to supply power to excitation source 4. In particular, an excitation source 4 may be included within enclosure 20 in those embodiments in which a detectable marker expressed by a transformed bacterium requires excitation from an external source in order to emit a detectable signal. For instance, in those embodiments in which a bacterium has been transformed to express GFP, an excitation signal may be provided to the marker in order for the marker to emit an optically detectable signal. Accordingly, in such an embodiment, a sensor may include an excitation source 4. In other embodiments, however, for instance in those embodiments in which an optically detectable signal is provided according to a luciferase/luciferin interaction, an excitation source 4 need not be included in enclosure 20.

In the illustrated exemplary configuration, including an excitation source 4, excitation source 4 may correspond to a light emitting diode (LED), however, again, such source may vary and may include, but is not limited to, laser diodes and incandescent light sources. Excitation source 4 may correspond to a white light source, a non-white multi-wavelength source, or a single wavelength source, as desired or required. In a preferred exemplary configuration, an LED may be selected due to the low power consumption of such sources. The wavelength of the excitation energy supplied by excitation source 4 may be of any suitable wavelength, from infrared (IR) to ultraviolet (UV). In general, the preferred excitation energy wavelength may depend upon the specific design of the detectable marker(s). For instance, in those embodiments in which a single type of bacteria is targeted, or alternatively where a plurality of bacterial pathogens are targeted, and different bacteriophages have been engineered to all encode the same detectable marker, an excitation source 4 may provide a single excitation wavelength. In other embodiments, however, for instance when a plurality of different detectable markers may be detected, and some or all of the markers respond to a different excitation wavelength, an excitation source may provide multiple wavelengths, either through combination of signals from a plurality of single wavelength sources or through a single, incoherent source, as desired.

Excitation energy source 4 is optically coupled to an optical fiber 6 as illustrated. Optical fiber 6 is configured to extend externally from enclosure 20 to the field of inquiry, e.g., within a surgical site or other wound. It should be appreciated that although a single optical fiber 6 is illustrated in FIG. 4, such is not a specific limitation of the present disclosure as a sensor may include multiple fibers in a single cable in alternate embodiments, and as discussed above. Those of ordinary skill in the art will appreciate that a single excitation energy source may be optically coupled to a plurality of optical fibers through utilization of suitable beam splitters, mirrors, and so forth.

Moreover, as discussed previously, plural excitation energy sources may be used. In such a configuration, each excitation source may be optically coupled to one or more optical fibers such that multiple excitation wavelengths may be delivered to the field of enquiry.

Housed within enclosure 20 is an optical detector 8 coupled to optical fiber 6. Optical detector 8 may correspond to a photodiode, a photoresistor, or the like. Optical detector 8 may include optical filters, beam splitters, and so forth that may remove background light and reduce the total input optical signal at the detector 8 to one or more diagnostically relevant emission peaks. Optical detector 8 may produce a signal proportional to targeted emission peaks and couple such signal to line 10 for transmission to signal processor 12.

Signal processor 12 may include a microprocessor configured to evaluate the strength or other characteristics of the output signal received over line 10 to, e.g., correlate the optical signal to the concentration of bacteria at the detection site and to produce a detection signal that may be coupled to line 14 for passage to a signaling device 16. Accordingly, if the detection signal reaches a predetermined threshold value, corresponding to a known concentration of the target pathogen, a detectable signal may be initiated at signaling device 16. In an exemplary configuration, a detectable signal may initiate a visible or audible signal within or at the surface of the enclosure 20 by way of signaling device 16 that may be detected by the wearer. For instance, a visible signal may optionally include utilization of a liquid crystal diode (LCD) device, or an equivalent thereof, that may provide the signal as a readable output. For example, a visual signal may be provided at a surface of the device 100 as an instruction such as, for instance, "CALL YOUR DOCTOR", "VISIT HOSPITAL," or the like.

In addition to or alternative to a visual and/or audible signal at the enclosure 20 itself, signaling device 16 may include a transmitter portion that, upon initiation of the detectable signal, may transmit an electromagnetic signal to receiver 18. Receiver 18 may be remote from the signaling device 16. For instance, receiver 18 may be on the wearer's body at a distance from the signaling device 16, at a location apart from the wearer's body that may be conveniently chosen by the wearer, e.g., within the wearer's home, office, or the like, or may be at a monitoring facility, for instance at a medical facility, such that appropriate medical personal may be quickly informed of the change in status of the patient's site of inquiry. In alternative embodiments, the detectable signal may be transmitted to multiple receivers, so as to inform both the wearer and others (e.g., medical personnel) of the change in status of a site. Transmission of a signal to a remote site may be carried out with a radio frequency transmission system or with any other wireless-type transmission system, as is generally known in the art. For instance, a wireless telephone or Internet communications system may be utilized to transmit a signal to a remote location according to known methods.

Wireless transmission systems as may be utilized in conjunction with disclosed devices and methods may include, for example, components and systems as disclosed in U.S. Pat. Nos. 6,289,238 to Besson, et al., 6,441,747 to Khair, et al., 6,802,811 to Slepian, 6,659,947 to Carter, et al., and 7,294,105 to Islam, all of which are incorporated in their entirety by reference.

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A portable device for detecting the presence or amount of a pathogenic bacterium that is a source of a hospital acquired infection comprising:
   a portable enclosure containing a power source, an optical detector, a signal processor, and a signaling device for emitting a signal upon detection of the pathogenic bacterium in an environment;
   a connecting device for attaching the enclosure to the clothing or body of a wearer;
   a fiber optic cable for inserting into the environment, the fiber optic cable being in optical communication with the optical detector, the fiber optic cable extending for a length exterior to the enclosure; and
   a delivery vehicle on at least a portion of the exterior surface of the fiber optic cable, the delivery vehicle containing a recombinant bacteriophage carrying exogenous genetic material encoding a protein that directly or indirectly produces an optically detectable signal.

2. The device of claim 1, the enclosure further including a transmitter for transmitting a signal containing information regarding the presence or amount of the bacterium in the environment to a receiver.

3. The device of claim 1, wherein the delivery vehicle is a degradable polymeric matrix.

4. The device of claim 1, the portable enclosure further comprising an excitation source in optical communication with the fiber optic cable.

5. The device of claim 1, the portable enclosure further comprising a transmitter in electrical communication with the signaling device, wherein the signal emitted from the signaling device is subsequently transmitted from the transmitter.

6. The device of claim 5, further comprising a receiver, wherein the transmitter is in wireless communication with the receiver.

7. The device of claim 1, wherein the signaling device emits a plurality of signals upon detection of the pathogenic bacterium in an environment.

8. The device of claim 1, wherein the connecting device is for connecting the enclosure to a piece of clothing.

9. The device of claim 1, wherein the connecting device is for connecting the enclosure to a wearer's skin.

10. The device of claim 1, wherein the protein is a green fluorescent protein or a color variant thereof.

11. The device of claim 1, wherein the protein is luciferase.

* * * * *